US005565519A

United States Patent [19]

Rhee et al.

[11] Patent Number: 5,565,519
[45] Date of Patent: Oct. 15, 1996

[54] CLEAR, CHEMICALLY MODIFIED COLLAGEN-SYNTHETIC POLYMER CONJUGATES FOR OPHTHALMIC APPLICATIONS

[75] Inventors: Woonza M. Rhee, Palo Alto; Prema R. Rao, Los Gatos; George H. Chu, Cupertino; Frank A. DeLustro, Belmont, all of Calif.

[73] Assignee: Collagen Corporation, Palo Alto, Calif.

[21] Appl. No.: 147,227

[22] Filed: Nov. 3, 1993

Related U.S. Application Data

[63] Continuation-in-part of Ser. No. 922,541, Jul. 30, 1992, Pat. No. 5,328,955, which is a continuation-in-part of Ser. No. 433,441, Nov. 14, 1989, Pat. No. 5,162,430, which is a continuation-in-part of Ser. No. 274,071, Nov. 21, 1988, abandoned.

[51] Int. Cl.$^6$ ............................ C08G 63/48; C08G 63/91
[52] U.S. Cl. ........................................... 525/54.1; 523/113
[58] Field of Search ............................ 525/54.1; 523/113

[56] References Cited

U.S. PATENT DOCUMENTS

| | | | |
|---|---|---|---|
| 3,619,371 | 11/1971 | Crook et al. | 525/54.1 |
| 3,788,948 | 1/1974 | Kagedal et al. | 525/54.1 |
| 3,876,501 | 4/1975 | Hanushewsky | 3/1 |
| 3,949,073 | 4/1976 | Daniels et al. | 424/177 |
| 3,960,830 | 6/1976 | Bayer et al. | 530/351 |
| 4,002,531 | 1/1977 | Royer | 435/179 |
| 4,055,635 | 10/1977 | Green et al. | 424/78 |
| 4,088,538 | 5/1978 | Schneider | 435/179 |
| 4,164,559 | 8/1979 | Miyata et al. | 530/350 |
| 4,179,337 | 12/1979 | Davis | 435/181 |
| 4,192,021 | 3/1980 | Deibig et al. | 3/1.9 |
| 4,261,973 | 4/1981 | Lee et al. | 424/78 |
| 4,301,144 | 11/1981 | Iwashita et al. | 525/54.1 |
| 4,314,380 | 2/1982 | Miyata et al. | 3/1.9 |
| 4,357,274 | 11/1982 | Werner | 530/350 |
| 4,412,989 | 11/1983 | Iwashita et al. | 525/54.1 |
| 4,414,147 | 11/1983 | Klibanov et al. | 530/356 |
| 4,415,665 | 11/1983 | Mosbach et al. | 435/179 |
| 4,424,208 | 1/1984 | Wallace et al. | 424/177 |
| 4,451,568 | 5/1984 | Schneider et al. | 435/179 |
| 4,488,911 | 12/1984 | Luck et al. | 106/161 |
| 4,495,285 | 1/1985 | Shimizu et al. | 435/215 |
| 4,496,698 | 1/1985 | Mitra | 525/54.1 |
| 4,557,764 | 12/1985 | Chu | 106/161 |
| 4,563,490 | 1/1986 | Stol et al. | 530/356 |
| 4,582,640 | 4/1986 | Smestad et al. | 530/356 |
| 4,592,864 | 6/1986 | Miyata et al. | 530/356 |
| 4,642,117 | 2/1987 | Nguyen et al. | 623/11 |
| 4,678,468 | 7/1987 | Hiroyoshi | 623/1 |
| 4,687,820 | 8/1987 | Hou et al. | 525/54.1 |
| 4,689,399 | 8/1987 | Chu | 530/356 |
| 4,703,108 | 10/1987 | Silver et al. | 530/356 |
| 4,732,863 | 3/1988 | Tomasi et al. | 436/547 |
| 4,737,544 | 4/1988 | McCain et al. | 424/409 |
| 4,745,180 | 5/1988 | Moreland et al. | 530/351 |
| 4,766,106 | 8/1988 | Katre et al. | 524/12 |
| 4,828,563 | 5/1989 | Muller-Lierhern | 623/16 |
| 4,847,325 | 7/1989 | Shadle et al. | 525/54.1 |
| 4,923,467 | 5/1990 | Thompson | 623/5 |
| 4,935,465 | 6/1990 | Garman | 525/54.1 |
| 4,979,959 | 12/1990 | Guire | 623/66 |
| 5,156,622 | 10/1992 | Thompson | 623/5 |
| 5,162,430 | 11/1992 | Rhee et al. | 525/54.1 |
| 5,163,956 | 11/1992 | Liu et al. | 623/4 |
| 5,196,027 | 3/1993 | Thompson et al. | 623/5 |
| 5,201,764 | 4/1993 | Kelman et al. | 623/6 |

FOREIGN PATENT DOCUMENTS

| | | |
|---|---|---|
| 098110 | 1/1984 | European Pat. Off. |
| 200574 | 11/1986 | European Pat. Off. |
| 247860 | 12/1987 | European Pat. Off. |
| 90120636.7 | 8/1991 | European Pat. Off. |
| 466300 | 1/1992 | European Pat. Off. |
| 92303469.8 | 10/1992 | European Pat. Off. |
| 4-227265 | 8/1992 | Japan . |
| WO84/01106 | 3/1984 | WIPO . |
| WO87/04078 | 7/1987 | WIPO . |
| PCT/US89/05351 | 5/1990 | WIPO . |
| PCT/US93/06292 | 1/1994 | WIPO . |

OTHER PUBLICATIONS

Document Number 07/907,518 Rhee et al. Jul. 2, 1992.

Abuchowski et al., "Cancer Therapy with Chemically Modified Enzymes. I. Antitumor Properties of Polyethylene Glycol–Asparaginase Conjugates," *Cancer Biochem Biophys* (1984) 7:175–86.

Bendich, A. et al., "Immunological Effects of Native and Polyethylene Glycol–Modified Asparaginases from *Vibrio Succinogenes* and *Escherichia Coli* in Normal and Tumour–Bearing Mice," *Clin Exp Immunol* (1982) 48:273–78.

Chen, R. H. L. et al., "Properties of Two Urate Oxidases Modified by the Covalent Attachment of Poly(ethylene Glycol)," *Biochim Biophys Acta* (1981) 660:293–98.

(List continued on next page.)

*Primary Examiner*—Nathan M. Nutter
*Attorney, Agent, or Firm*—Kathi Rafayko; Shirley L. Church

[57] ABSTRACT

Various forms of chemically modified collagen are covalently crosslinked with activated synthetic hydrophilic polymers to form optically clear biocompatible conjugates useful in a variety of medical applications, particularly in ophthalmic devices. The chemically modified collagen is in substantially nonfibrillar form at pH 7 and is preferably succinylated or methylated collagen. The synthetic hydrophilic polymer is preferably an activated polymeric glycol, most preferably, a di- or multifunctionally activated polyethylene glycol. Materials and devices formed with the chemically modified collagen-synthetic polymer conjugates have good optical clarity, mechanical strength, and moldability.

4 Claims, 3 Drawing Sheets

OTHER PUBLICATIONS

Chvapil, M. et al., "Some Chemical and Biological Characteristics of a New Collagen–Polymer Compound Material," *J Biomed Mater Res* (1969) 3:315–32.

Davis et al., "Hypouricaemic Effect of Polyethyleneglycol Modified Urate Oxidase," *Lancet* (1981) 2:281–83.

Inada et al., "Ester Synthesis Catalyzed by Polyethylene Glycol–Modified Lipase in Benzene," *Biochem & Biophys Res Comm* (1984) 122:845–50.

Llyod et al., "Coupling of Acrylic Polymer and Collagen by Use of a Water–Soluble Carbodiimide," *J Polymer Sci. Chem Ed.* (1979) 17:3473–3483.

Nishida et al., "Hypouricaemic Effect after Oral Administration in Chickens of Polyethylene Glycol–Modified Uricase Entrapped in Liposomes," *J Pharm Pharmacol* (1984) 36:354–55.

Pyatak, P. S. et al., "Preparation of a Polyethylene Glycol: Superoxide Dismutase Adduct, and an Examination of it Blood Circulating Life and Anti–Inflammatory Activity," *Res Com Chem Path Pharmacol* (1980) 29:113–27.

Ramshaw, J. A. M. et al., "Precipitation of Collagens by Polyethylene Glycols," *Anal Biochem* (1984) 141:361–65.

Savoca, K. V. et al., "Preparation of a Non–immunogenic Arginase by the Covalent Attachment of Polyethylene Glycol," *Biochem Biophys Acta* (1979) 578:47–53.

Takahashi et al., "A Chemical Modification to Make Horseradish Peroxidase Soluble and Active in Benzene," *Biochem & Biophys Res Comm* (1984) 121:261–65.

Viau, A. T. et al. "Safety Evaluation of Free Radical Scavengers PEG–Catalase and PEG–Superoxide Dismutase," *J Free Rad in Bio & Med* (1986) 2:283–288.

Viau, A. T. et al. "Toxicologic Studies of a Conjugate of Asparaginase and Polyethylene Glycol in Mice, Rats, and Dogs," *Am J Vet Res* (1986) 47:1398–401.

Wieder, K. J. et al., "Some Properties of Polyethylene Glycol: Phenylalanine Ammonia–Lyase Adducts," *J Biol Chem* (1979) 254:12579–87.

CLEAR, CHEMICALLY MODIFIED COLLAGEN-SYNTHETIC POLYMER CONJUGATES FOR OPHTHALMIC APPLICATIONS

CROSS-REFERENCES

This application is a continuation-in-part of U.S. application Ser. No. 07/922,541, filed Jul. 30, 1992 and now U.S. Pat. No. 5,328,955, which is a continuation-in-part of U.S. application Ser. No. 07/433,441, filed Nov. 14, 1989 and now U.S. Pat. No. 5,162,430, issued Nov. 10, 1992, which is a continuation-in-part of U.S. application Ser. No. 07/274,071, filed Nov. 21, 1988, subsequently abandoned, which applications and issued patents are incorporated herein by reference in full and to which we claim priority under 35 USC §120.

FIELD OF THE INVENTION

This invention relates to biocompatible conjugates comprising chemically modified collagens, which are in substantially nonfibrillar form at pH 7, covalently bound to activated synthetic hydrophilic polymers, which conjugates are formulated to be optically clear and have superior mechanical strength compared to non-crosslinked formulations, which make them suitable for use in ophthalmic devices.

BACKGROUND OF THE INVENTION

Daniels et al, U.S. Pat. No. 3,949,073, disclosed the preparation of soluble collagen by dissolving tissue in aqueous acid, followed by enzymatic digestion. The resulting atelopeptide collagen is soluble, and substantially less immunogenic than unmodified collagen. It may be injected into suitable locations of a subject with a fibril-formation promoter (described as a polymerization promoter in the patent) to form fibrous collagen implants in situ, for augmenting hard or soft tissue. This material is now commercially available from Collagen Corporation (Palo Alto, Calif.) under the trademark Zyderm® Collagen Implant.

Miyata et al, U.S. Pat. No. 4,164,559, disclosed an ophthalmic drug delivery system comprising a chemically modified collagen thin membrane carrier. While these materials are clear, they do not have the mechanical strength required for ophthalmic devices such as lenticules, which are intended for long-term in vivo use.

Luck et al, U.S. Pat. No. 4,488,911, disclosed a method for preparing collagen in solution (CIS), wherein native collagen is extracted from animal tissue in dilute aqueous acid, followed by digestion with an enzyme such as pepsin, trypsin, or Pronase®, a trademark of American Hoechst Corporation, Somerville, N.J. The enzymatic digestion removes the telopeptide portions of the collagen molecules, providing "atelopeptide" collagen in solution. The atelopeptide CIS so produced is substantially nonimmunogenic, and is also substantially non-crosslinked due to loss of the primary crosslinking regions. The CIS may then be precipitated by dialysis in a moderate shear environment to produce collagen fibers which resemble native collagen fibers. The precipitated, reconstituted fibers may additionally be crosslinked using a chemical agent (for example, aldehydes such as formaldehyde and glutaraldehyde), heat, or radiation. The resulting products are suitable for use in medical implants due to their biocompatability and reduced immunogenicity.

Wallace et al, U.S. Pat. No. 4,424,208, disclosed an improved collagen formulation suitable for use in soft tissue augmentation. Wallace's formulation comprises reconstituted fibrillar atelopeptide collagen (for example, Zyderm® Collagen) in combination with particulate, crosslinked atelopeptide collagen dispersed in an aqueous medium. The addition of particulate crosslinked collagen improves the implant's persistence, or ability to resist shrinkage following implantation.

Smestad et al, U.S. Pat. No. 4,582,640. disclosed a glutaraldehyde crosslinked atelopeptide CIS preparation (GAX) suitable for use in medical implants. The collagen is crosslinked under conditions favoring interfiber bonding rather than intrafiber bonding, and provides a product with higher persistence than non-crosslinked atelopeptide collagen. Said product is commercially available from Collagen Corporation under the trademark Zyplast® Collagen Implant.

Nguyen et al, U.S. Pat. No. 4,642,117, disclosed a method for reducing the viscosity of atelopeptide CIS by mechanical shearing. Reconstituted collagen fibers are passed through a fine-mesh screen until viscosity is reduced to a practical level for injection.

Nathan et al, U.S. Pat. No. 4,563,350, disclosed osteoinductive bone repair compositions comprising an osteoinductive factor, at least 5% nonreconstituted (afibrillar) collagen, and the remainder reconstituted collagen and/or mineral powder (e.g., hydroxyapatite). CIS may be used for the nonreconstituted collagen, and Zyderm® Collagen Implant (ZCI) is preferred for the reconstituted collagen component. The material is implanted in bone defects or fractures to speed ingrowth of osteoclasts and promote new bone growth.

Chu, U.S. Pat. No. 4,557,764, disclosed a "second nucleation" collagen precipitate which exhibits a desirable malleability and putty-like consistency. Collagen is provided in solution (e.g., at 2–4 mg/mL), and a "first nucleation product" is precipitated by rapid titration and centrifugation. The remaining supernatant (containing the bulk of the original collagen) is then decanted and allowed to stand overnight. The precipitated second nucleation product is collected by centrifugation.

Chu, U.S. Pat. No. 4,689,399, disclosed a collagen membrane preparation, which is prepared by compressing and drying a collagen gel. The resulting product has high tensile strength.

Silver et al., U.S. Pat. No. 4,703,108, disclosed the preparation of a sponge prepared by crosslinking insoluble/ collagen using dehydrothermal means or by using cyanamide. Berg et at., U.S. Pat. No. 4,837,285, disclosed the preparation of collagen in bead form for soft tissue augmentation. Brodsky et al., U.S. Pat. No. 4,971,954, have disclosed a method of crosslinking collagen using ribose or other reducing sugars.

Miyata et al., Japartese patent application 63-256512, published Aug. 17, 1992, discloses a composition comprised of atelopeptide collagen linked to a polyepoxy compound. The composition is injected into the body to obtain sustained skin-lifting effects.

J. A. M. Ramshaw et al, *Anal Biochem* (1984) 141:361–65, and PCT application WO87/04078, disclosed the precipitation of bovine collagen (types I, II, and III) from aqueous PEG solutions, where there is no binding between collagen and PEG.

Werner, U.S. Pat. No. 4,357,274, disclosed a method for improving the durability of sclero protein (e.g., brain meninges) by soaking the degreased tissue in hydrogen peroxide or polyethylene glycol for several hours prior to lyophilization. The resulting modified whole tissue exhibits increased persistence.

Hiroyoshi, U.S. Pat. No. 4,678,468, disclosed the preparation of polysiloxane polymers having an interpenetrating network of water-soluble polymer dispersed within. The water-soluble polymer may be a collagen derivative, and the polymer may additionally include heparin. The polymers are shaped into artificial blood vessel grafts, which are designed to prevent clotting.

Other patents disclose the use of collagen preparations incorporating bone fragments or minerals. For example, Miyata et al, U.S. Pat. No. 4,314,380, disclosed a bone implant prepared by baking animal bone segments, then soaking the baked segments in a solution of atelopeptide collagen. Deibig et at, U.S. Pat. No. 4,192,021, disclosed an implant material which comprises powdered calcium phosphate in a pasty formulation with a biodegradable polymer (which may be collagen). Commonly owned U.S. application Ser. No. 06/855,004, filed Apr. 22, 1986, now abandoned, disclosed a particularly effective bone repair material comprising autologous bone marrow, collagen, and particulate calcium phosphate in a solid, malleable formulation.

There are several references in the an to proteins modified by covalent conjugation to polymers to alter the solubility, antigenicity, and biological clearance of the protein. For example, U.S. Pat. No. 4,261,973 disclosed the conjugation of several allergens to PEG or PPG (polypropylene glycol) to reduce the proteins' immunogenicity. U.S. Pat. No. 4,301,144 disclosed the conjugation of hemoglobin with PEG and other polymers to increase the protein's oxygen-carrying capability. EP O98110 disclosed coupling an enzyme or interferon to a polyoxyethylene-polyoxypropylene (POE-POP) block polymer to increase the protein's half-life in serum. U.S. Pat. No. 4,179,337 disclosed conjugating hydrophilic enzymes and insulin to PEG or PPG to reduce immunogenicity. Davis et al, *Lancet* (1981) 2:281–83, disclosed the enzyme uricase modified by conjugation with PEG to provide uric acid metabolism in serum having a long half-life and low immunogenicity. Nishida et al, *J Pharm Pharmacol* (1984) 36:354–55, disclosed PEG-uricase conjugates administered orally to chickens, demonstrating decreased serum levels of uric acid. Inada et al, *Biochem & Biophys Res Comm* (1984) 122:845–50 disclosed lipoprotein lipase conjugated with PEG to render it soluble in organic solvents. Takahashi et al, *Biochem & Biophys Res Comm* (1984) 121:261–65, disclosed HRP conjugated with PEG to render the enzyme soluble in benzene. Abuchowski et al, *Cancer Biochem Biophys* (1984) 7:175–86, disclosed that enzymes such as asparaginase, catalase, uricase, arginase, trypsin, superoxide dismutase, adenosine deaminase, phenylalanine ammonia-lyase and the like conjugated with PEG exhibit longer half-lives in serum and decreased immunogenicity. However, these references are essentially concerned with modifying the solubility and biological characteristics of proteins administered in low concentrations in aqueous solution.

M. Chvapil et al, *J Biomed Mater Res* (1969) 3:315–32, disclosed a composition prepared from collagen sponge and a crosslinked ethylene glycol monomethacrylate-ethylene glycol dimethacrylate hydrogel. The collagen sponge was prepared by lyophilizing an aqueous mixture of bovine hide collagen and methylglyoxal, a tanning agent. The sponge-hydrogel composition was prepared by polymerizing ethylene glycol monomethacrylate and ethylene glycol dimethacrylate in the sponge.

A series of related patents disclose various types of collagen-containing materials. The patents are U.S. Pat. Nos. 4,703,108, issued Oct. 27, 1987; 4,861,714, issued Aug. 29, 1989; 4,863,856, issued Sep. 5, 1989; 4,925,924, issued May 15, 1990; 4,970,298, issued Nov. 13, 1990; and 4,997,753, issued Mar. 5, 1991. All of these patents disclose collagen materials wherein type I, II, and III collagens are contacted with a crosslinking agent selected from the group consisting of a carbodiimide or a succinimidyl active ester. Various types of treatment may be carried out prior to or after crosslinking in order to form particular types of desired materials such as sponges and/or sheets.

In commonly owned U.S. Pat. No. 5,162,430, issued Nov. 10, 1992, we described conjugates whereby atelopeptide collagen is covalently crosslinked with synthetic hydrophilic polymers such as polyethylene glycol. Such conjugates are useful for a variety of applications, such as soft tissue augmentation and the formation of implants useful in bone repair. In U.S. application Ser. No. 07/922,541, we disclose various activated forms of polyethylene glycol and various linkages which can be used to produce collagen-synthetic polymer conjugates having a range of physical and chemical properties. We now describe collagen-synthetic polymer conjugates formed using chemically modified forms of collagen, which impart to the conjugate specific properties, such as optical clarity and mechanical strength, making the conjugates particularly useful in devices for use in ophthalmic applications.

SUMMARY OF THE INVENTION

Chemically modified collagen is covalently crosslinked with an activated synthetic hydrophilic polymer to form a conjugate. The conjugate can be formulated into compositions having sufficient clarity that the compositions can be used to produce various ophthalmic devices and materials. The synthetic hydrophilic polymer is preferably various forms of activated polymeric glycols, most preferably polyethylene glycol. The chemically modified collagen is preferably succinylated collagen, produced by reacting collagen with succinic anhydride, or methylated collagen, produced by reacting collagen with methanol.

Furthermore, different forms of chemically modified collagens (for example, methylated collagen and succinylated collagen) can be mixed in varying ratios prior to covalent crosslinking to produce transparent materials having a range of physical properties and different degrees of crosslinking.

The present invention provides materials comprised of the covalently bound chemically modified collagen-synthetic polymer conjugates which have good optical clarity (i.e., greater than 90% transmittance of light having a wavelength of 410 nm), mechanical strength, and moldability.

The chemically modified collagen-synthetic polymer conjugates of the present invention have optical properties such that the conjugates can be used to produce ophthalmic devices.

An advantage of the invention is that the chemically modified collagen-synthetic polymer conjugates can be used to produce products which are clear, strong, nonimmunogenic, and permeable to oxygen and other nutrients.

A feature of the invention is that the covalently bound chemically modified collagen-synthetic polymer conjugates are moldable and can be molded into an article which is sufficiently high in light transmittance that it may be considered clear, i.e., of optical quality.

These and other features of the present invention will become apparent to those persons skilled in the art upon reading the details of the structure, synthesis, and usage of the conjugates and clear articles made therewith as more fully set forth below.

DETAILED DESCRIPTION OF PREFERRED EMBODIMENTS OF THE INVENTION

Figure 1:
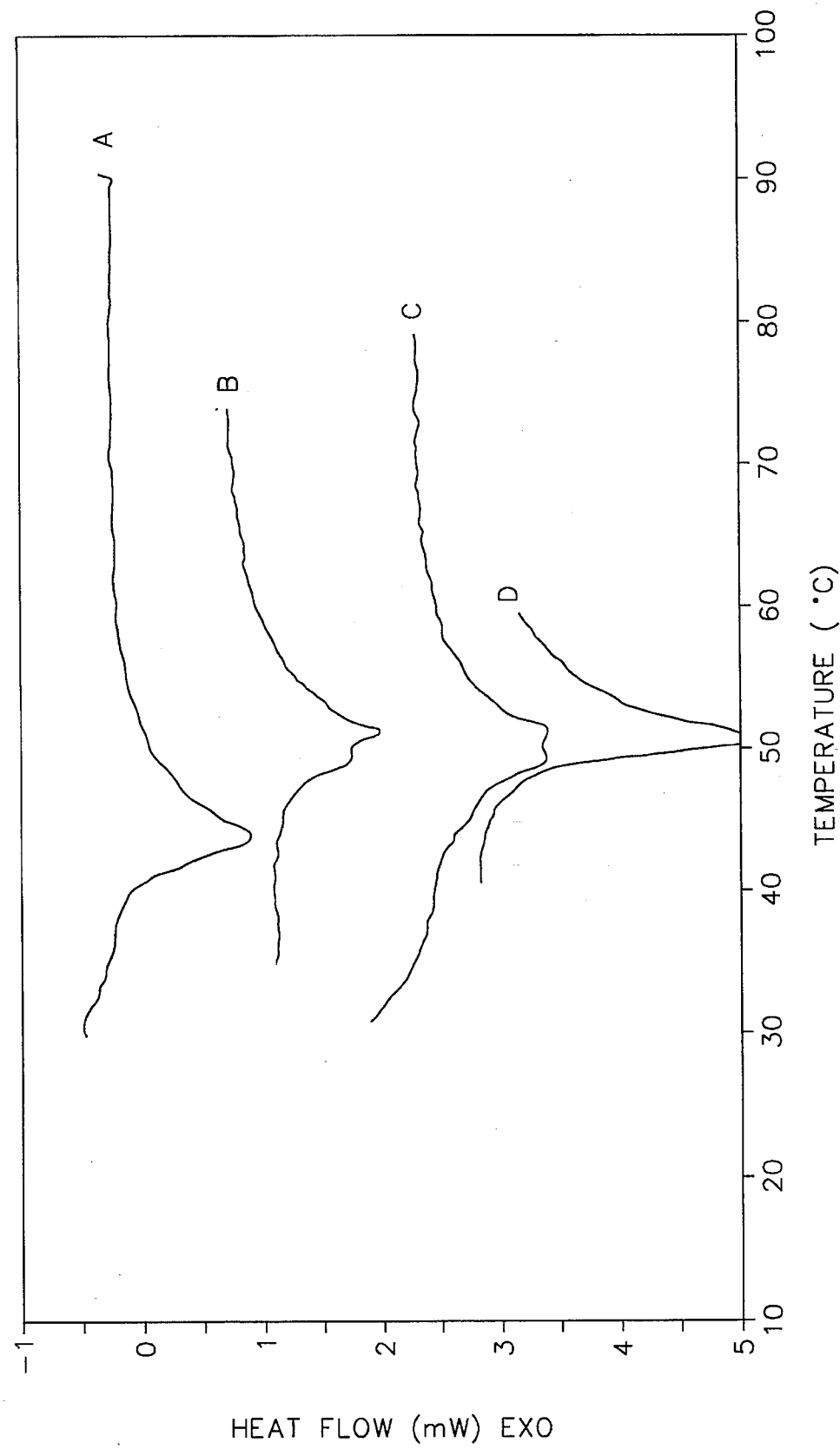
FIG. 1 shows differential scanning calorimetry (DSC) results for noncrosslinked succinylated collagen (Sample A) and succinylated collagen formulations containing 10, 20, 50, and 91 mg/ml S-PEG (Samples B, C, and D, respectively).

It must be noted that, as used in this specification and the appended claims, the singular forms "a", "an", and "the" include plural referrents unless the context clearly dictates otherwise. Thus, for example, reference to "a conjugate" includes one or more conjugate molecules, reference to "an article" includes one or more different types of articles known to those skilled in the art and reference to "the collagen" includes mixtures of different types of collagens and so forth.

Unless defined otherwise, all technical and scientific terms used herein have the same meaning as commonly understood by one of ordinary skill in the art to which this invention belongs. Although any methods and materials similar or equivalent to those described herein may be useful in the practice or testing of the present invention, only the preferred methods and materials are described below; it is not intended that the invention be limited to these preferred embodiments, however. The invention is intended to have the scope defined by the attached claims.

All publications mentioned herein are incorporated herein by reference to describe and disclose the subject matter for which it is cited.

Specific terminology of particular importance to the description of the present invention is defined below.

Definitions

The term "collagen" as used herein refers to all forms of collagen which can be used as starting materials, including those which have been recombinantly produced, extracted from naturally occurring sources, processed, or otherwise modified. Collagens may or may not be treated to remove the immunogenic telopeptide regions ("atelopeptide collagen"). Atelopeptide fibrillar collagen at approximately pH 7 is the preferred starting material to produce the chemically modified collagens which are covalently bound to synthetic hydrophilic polymers to produce the clear conjugates of the invention. Crosslinked collagen prepared using heat, radiation, or chemical agents such as glutaraldehyde is not preferred as a starting material for preparation of the compositions of the present invention. Collagen used in connection with the preferred embodiments of the invention is in a pharmaceutically pure form such that it can be incorporated into a human body for the intended purpose without generating any significant immune response. Collagen used to form a conjugate must form a conjugate which will allow the production of an ophthalmic device with acceptable optical properties.

The term "nonfibrillar collagen" refers to collagens in which the triple helical molecules do not aggregate to form fibers.

The term "succinylated collagen" refers to collagen which has been reacted with succinic anhydride or other anhydrides, resulting in acylation of the free amino groups on the collagen molecule. A method for preparing succinylated collagen is disclosed in U.S. Pat. No. 4,164,559, which is incorporated herein by reference.

The term "methylated collagen" refers to collagen which has been reacted with methanol or another water-soluble aliphatic alcohol such as ethanol, resulting in esterification of the free carboxyl groups on the collagen molecule. A method for preparing methylated collagen is also disclosed in U.S. Pat. No. 4,164,559.

Preferred synthetic polymers for use in the present invention are hydrophilic and are highly pure or are purified to a highly pure state such that the polymer is or is treated to become pharmaceutically pure so that it may be injected into a human patient. Most hydrophilic synthetic polymers can be rendered water-soluble by incorporating a sufficient number of oxygen (or less frequently nitrogen) atoms available for forming hydrogen bonds in aqueous solutions. Preferred synthetic polymers are hydrophilic, but not necessarily water-soluble. Hydrophilic synthetic polymers described in the preferred embodiments herein include activated forms of polyethylene glycol (PEG), polyoxyethylene, polymethylene glycol, polytrimethylene glycols, polyvinylpyrrolidones, and derivatives thereof, with activated PEG being particularly preferred. The synthetic polymers can be linear or multiply branched, be:at are typically not substantially crosslinked. Other suitable hydrophilic synthetic polymers include:, for example, polyoxyethylene-polyoxypropylene block polymers and copolymers. Polyoxyethylene-polyoxypropylene block polymers having an ethylenediamine nucleus (and thus having four ends) are commercially available and may be used in the practice of the invention. Naturally occurring polymers such as proteins, starch, cellulose, heparin, hyaluronic acid, derivatives thereof, and the like are expressly excluded from the scope of this definition. All suitable synthetic polymers will be nontoxic, noninflammatory, and nonimmunogenic when administered subcutaneously, and will preferably be essentially nondegradable in vivo over a period of at least several months. The hydrophilic synthetic polymer may increase the hydrophilicity of the conjugate, but does not render it water-soluble. The most preferred hydrophilic synthetic polymers include mono-, di-, and multifunctionally activated polymeric glycols. Monofunctionally activated polymeric glycols have only one reactive hydroxy group, while difunctionally activated polymeric glycols typically have two reactive groups, one at each end of the polymer chain. Monofunctionally activated polymeric glycols preferably have an average molecular weight between about 100 and about 15,000, more preferably between about 200 and about 8,000, and most preferably about 5,000. Difunctionally activated polymeric glycols preferably have an average molecular weight of between about 400 to about 40,000, most preferably about 3,000 to about 10,000. Multifunctionally activated polymeric glycols preferably have an average molecular weight between about 3,000 and 100,000.

Polymeric glycols can be rendered monofunctionally activated by forming an alkylene ether group at one end, for example. The alkylene ether group may be any suitable alkoxy radical having 1–6 carbon atoms, for example, methoxy, ethoxy, propoxy, 2-propoxy, butoxy, hexyloxy, and the like. Methoxy is presently preferred. Difunctionally activated polymeric glycols typically are prepared by constructing reactive hydroxy groups at the ends of the polymer. Multifunctionally activated synthetic polymers can be prepared using various techniques known in the art which provide active functional groups at various locations along the polymer. Multifunctionally activated synthetic polymers are capable of crosslinking the compositions of the invention, and may further be used to attach cytokines or growth factors to the nonfibrillar collagen-synthetic polymer conjugate.

The term "chemically conjugated" as used herein means attached through a covalent chemical bond. In the practice of the invention, a hydrophilic synthetic polymer and a chemically modified collagen may be covalently conjugated using a linking radical, so that the hydrophilic synthetic polymer and chemically modified collagen are each bound to the radical, but not directly to each other. The term "collagen-polymer" refers to collagen chemically conjugated to a synthetic hydrophilic polymer, within the meaning of this invention. For example, "PEG-collagen" or "collagen-PEG" denotes a composition of the invention wherein collagen is covalently conjugated to PEG. "Collagen-dPEG" is a subset of collagen-PEG and refers to collagen covalently conjugated to a difunctionally activated PEG, wherein the collagen molecules are crosslinked by means of the two functional ends of each PEG molecule. "Crosslinked collagen" refers to collagen in which collagen molecules are linked by covalent bonds with multifunctionally activated (including the difunctionally activated) synthetic hydrophilic polymers. The activated hydrophilic synthetic polymer may be "covalently conjugated" to the nonfibrillar collagen by means of a number of different types of chemical linkage. For example, the conjugation can be via an ester or a urethane linkage, but is more preferably by means of an ether linkage. An ether linkage is preferred in that it can be formed without the use of toxic chemicals and is not readily susceptible to hydrolysis in vivo.

Those of ordinary skill in the art will appreciate that synthetic polymers such as polyethylene glycol cannot be prepared practically to have exact molecular weights, and that the term "molecular weight" as used herein refers to the weight average molecular weight of a number of molecules in any given sample, as commonly used in the art. Thus, a sample of PEG 2,000 might contain a statistical mixture of polymer molecules ranging in weight from, for example, 1,500 to 2,500, with one molecule differing slightly from the next over a range. Specification of a range of molecular weight indicates that the average molecular weight may be any value between the limits specified, and may include molecules outside those limits. Thus, a molecular weight range of about 800 to about 20,000 indicates an average molecular weight of at least about 800, ranging up to about 20,000.

The term "available lysine residue" as used herein refers to lysine side chains exposed on the outer surface of collagen molecules, which have free amino groups capable of reacting with activated polymeric glycols. The number of available lysine residues may be determined by reaction with sodium 2,4,6-trinitrobenzenesulfonate (TNBS).

The terms "treat" and "treatment" as used herein refer to replacement, augmentation, repair, prevention, or alleviation of defects related to soft tissue and, in particular, ocular tissue. Additionally, "treat" and "treatment" also refer to the prevention, maintenance, or alleviation of disorders or disease using a biologically active protein coupled to or mixed with the conjugates or articles of the invention. Treatment of ocular tissue includes the augmentation of corneal tissue with an article having suitable ocular properties to effect refractive correction.

The terms "cytokine" and "growth factor" are used to describe biologically active molecules and active peptides (which may be either naturally occurring or synthetic) which aid in healing or regrowth of normal tissue and, in particular, ocular tissue. The function of cytokines and growth factors is two-fold: 1) they can incite local cells to produce new tissue, or 2) they can attract cells to the site in need of correction. As such, cytokine s or growth factors serve to encourage "biological anchoring" of any article or implant within the host tissue. As previously described, the cytokines and growth factors can either be admixed with the collagen-synthetic polymer conjugate or chemically coupled to the conjugate. For example, one may incorporate cytokines such as interferons (IFN), tumor necrosis factors (TNF), interleukins, colony stimulating factors (CSFs), or growth factors such as osteogenic factor extract (OFE), epidermal growth factor (EGF), transforming growth factor (TGF) alpha, TGF-β (including any combination of TGF-βs), TGF-β1, TGF-β2, platelet derived growth factor (PDGF-AA, PDGF-AB, PDGF-BB), acidic fibroblast growth factor (FGF), basic FGF, connective tissue activating peptides (CTAP), β-thromboglobulin, insulin-like growth factors, erythropoietin (EPO), nerve growth factor (NGF), and the like. Incorporation of cytokines, growth factors, and appropriate combinations of cytokines and growth factors can facilitate the regrowth and remodeling of a device or implant into normal tissue. Furthermore, one may chemically link the cytokines or growth factors to the collagen-polymer conjugate by employing a suitable amount of multifunctional polymer molecules during synthesis. The cytokines or growth factors may then be attached to the activated sites on the synthetic polymer by the same method used to attach PEG to collagen, or by another suitable method. By tethering cytokines or growth factors to the implant, the amount of cytokine or growth factor required to achieve a desired effect is substantially reduced. Devices incorporated with cytokines or growth factors may serve as effective controlled release drug delivery means. By varying the chemical linkage between the collagen and the synthetic polymer, it is possible to vary the effect with respect to the release of the cytokine. For example, when an "ester" linkage is used, the linkage is more easily broken under physiological conditions, allowing for sustained release of the growth factor from the matrix. However, when an "ether" linkage is used, the bonds are not easily broken and the cytokine or growth factor will remain in place for longer periods of time with its active sites exposed, providing a biological effect on the natural substrate for the active site of the protein. It is possible to include a mixture of conjugates with different linkages so as to obtain variations in the effect with respect to the release of the cytokine, i.e., the sustained release or controlled release effect can be modified to obtain the desired rate of release.

The term "effective amount" refers to the amount of composition required in order to obtain the effect desired. Thus, a "tissue growth-promoting amount" of a composition containing a cytokine refers to the amount of cytokine needed in order to stimulate tissue growth to a detectable degree. Tissue, in this context, includes any tissue, although ocular tissue is of particular interest in connection with the invention. The actual amount which is determined to be an effective amount will vary depending on factors such as the size, condition, sex, and age of the patient, and can be more readily determined by the caregiver.

The term "sufficient amount" as used herein is applied to the amount of carrier used in combination with the collagen-polymer conjugates of the invention. A sufficient amount is that amount which, when mixed with the conjugate, renders it in the physical form desired, for example, the conjugate may include a sufficient amount of liquid carrier for creating a malleable composition used to create a corneal implant having a gel-like consistency and texture similar to a soft contact lens. The flowable formulations generally include an amount of a carrier sufficient to render the composition smoothly flowable at room temperature. The amount of the carrier can be varied and adjusted depending on the particular conjugate used and the end result desired. Such adjustments will be apparent to those skilled in the art reading this disclosure.

The terms "implant" and "solid implant" refer to any solid object which is designed for insertion and use within the body, and includes ocular implants such as ophthalmic shields and corneal lenticules.

The term "in situ" as used herein means at the site of administration. For example, ophthalmic devices can be placed in the eye of a patient and drugs such as a cytokine dispersed therein will be released in situ.

The term "dehydrated" means that the material is air-dried or lyophilized to remove substantially all unbound water.

The term "aqueous mixture" of collagen includes liquid solutions, suspensions, dispersions, colloids, and the like containing collagen and water.

The term "clear" as used herein refers to an article which transmits at least 90% of the visible light directed at it at a thickness of 1 mm.

General Method

In order to produce the ophthalmic devices of the invention, it is necessary to produce chemically modified collagen-synthetic polymer conjugates of the kind previously described, from which the devices can be fabricated. In order to produce such conjugates, it is necessary to covalently bind chemically modified nonfibrillar collagen to an activated synthetic hydrophilic polymer such as, for example, an activated polymeric glycol. In accordance with one preferred method, (a) collagen is chemically modified by succinylation, methylation, or deamidation to produce collagen which is substantially nonfibrillar at pH 7, (b) the hydrophilic synthetic polymer is activated, and (c) the activated synthetic polymer is allowed to react with the chemically modified collagen, resulting in the formation of covalent crosslinks between the synthetic polymer and the collagen.

Chemical Modification of Fibrillar Collagen to Produce Nonfibrillar Collagen Suitable collagens for use as starting materials to produce the chemically modified collagen-synthetic polymer conjugates of the invention include all types of pharmaceutically useful collagens, preferably types I, II, and III. Collagens may be soluble (for example, commercially available Vitrogen® 100 collagen-in-solution, a trademark of Celtrix Pharmaceuticals, Santa Clara, Calif.), and may or may not have the telopeptide regions. The collagen may be reconstituted fibrillar atelopeptide collagen, for example, Zyderm® Collagen Implant (ZCI), a trademark of Collagen Corporation, Palo Alto, Calif., or atelopeptide collagen in solution (CIS). Various forms of collagen are available commercially, or may be prepared by the processes described in, for example, U.S. Pat. Nos. 3,949,073; 4,488,911; 4,424,208; 4,582,640; 4,642,117; 4,557,764; and 4,689,399, all incorporated herein by reference. Fibrillar atelopeptide reconstituted collagen is the presently preferred starting material.

Unmodified collagen, which is in fibrillar form at pH 7, is an opaque whitish viscous fluid unsuitable for use in the ophthalmic devices of the invention. Unmodified collagen has a net neutral charge at pH 7. Fiber formation occurs as a result of ionic interactions between opposite charges on various parts of the collagen molecule. Ionic interactions between collagen molecules causes the linear molecules to assemble into thick fibers.

As disclosed in U.S. Pat. No. 4,164,559, succinylated collagen is produced by reacting fibrillar collagen with succinic anhydride. Reaction of fibrillar collagen with succinic anhydride results in acylation of the free amino groups on the lysine residues of the collagen molecule. Other acylating agents that can be used include other anhydrides, such as acetic anhydride. Acylation of the amino groups results in the succinylated collagen molecules having a net negative charge at pH 7, preventing the ionic interactions which result in fiber formation. However, in an acidic environment, the negative charges are balanced by the free $H^+$ ions in the solution, resulting in a net neutral charge for the molecule and allowing fiber formation to occur. Succinylated collagen is in substantially nonfibrillar form above pH 5.5.

It must be pointed out that complete succinylation will result in acylation of all of the free amino groups on the lysine residues, which would leave no free amino groups available for crosslinking with the synthetic hydrophilic polymer. The collagen should therefore be incompletely succinylated, leaving at least a minimum percentage of amino groups available for covalent crosslinking with the activated synthetic polymer. The degree of succinylation can be controlled by carefully controlling the relative amounts of succinic acid reacted with the collagen. The preferred degree of succinylation is in the range of 25 to 50%, meaning that 25 to 50% of the available amino groups on the lysine residues of the collagen molecule are succinylated. Collagen succinylated to such a degree will possess an adequate number of sites for covalent crosslinking with the activated synthetic polymer and still result in a crosslinked material having the desired degree of clarity. Collagen succinylated at a level significantly below 25% may not be clear or stable. The percentage of free lysine residues available for crosslinking with the activated synthetic hydrophilic polymer can be determined by reaction with TNBS (e.g., 75% free lysine residues indicates that an average of approximately 25% of amino groups on the lysine residues of the collagen molecules in the sample are succinylated).

In one preferred method, collagen-in-solution (pH 2) is adjusted to pH 9 to produce fibrillar collagen, which is then reacted with succinic anhydride to produce succinylated collagen. The pH of the resulting succinylated collagen is subsequently adjusted to 5 or less, causing the succinylated collagen to precipitate, i.e., form fibers. The precipitated succinylated collagen is then concentrated by centrifugation. At this point, any unreacted fibrillar collagen is in solution (because of the low pH) and is discarded with the supernatant, leaving only precipitated succinylated collagen. The pH of the concentrated succinylated collagen is adjusted to 7 to cause the collagen fibers to disassemble, resulting in non-fibrillar collagen. The resulting succinylated collagen is then adjusted to the desired collagen concentration by adding water.

As disclosed in U.S. Pat. No. 4,164,559, methylated collagen is prepared by reacting fibrillar collagen with methanol. Reaction of fibrillar collagen with methanol (or other water-soluble aliphatic alcohol such as ethanol) results in esterification of free carboxyl groups on the collagen. Esterification of the carboxyl groups results in the methylated collagen molecules having a net positive charge at pH 7, preventing the ionic interactions which result in fiber formation. However, in a basic environment, the positive charges are balanced by the free OH$^-$ ions in the solution, resulting in a net neutral charge for the molecule and allowing fiber formation to occur. Methylated collagen is in substantially nonfibrillar form below pH 9.

Reaction with methanol does not affect the free amino groups on the collagen; therefore, it is possible to use collagen methylated to a level as high as 100% to form the conjugates of the invention. The degree of methylation can be controlled by limiting the reaction time of the methanol with the collagen.

In one preferred method, fibrillar collagen, such as Zyderm® I (35 mg/ml) or Zyderm II (65 mg/ml) Collagen (both available from Collagen Corporation, Palo Alto, Calif.), is lyophilized to produce freeze-dried collagen, which is subsequently chopped into small pieces. The chopped, freeze-dried fibrillar collagen is reacted with anhydrous acidic methanol and incubated at room temperature for 2 to 7 days to produce methylated collagen. The excess methanol is subsequently evaporated off and the resulting methylated collagen lyophilized and dialyzed. The collagen concentration of the methylated collagen may be adjusted at this point.

Succinylation or methylation of the collagen molecule provides collagen which is substantially nonfibrillar and, therefore, clear at physiological pH, in contrast to unmodified collagen, which is fibrillar and milky white at physiological pH. However, as described previously, the chemically modified collagens themselves do not have the mechanical strength or physical properties required to form ophthalmic devices intended for long-term use in the eye. Further, the chemically modified collagens are inherently more unstable than unmodified fibrillar collagen due to the stability imparted by the fibrillar structure. However, reaction of the chemically modified collagens with activated synthetic hydrophilic polymers provides stable, covalently crosslinked conjugates having the mechanical strength and physical characteristics required for use in the ophthalmic devices of the invention.

Activation of Polyethylene Glycol (PEG)

The first step in forming the conjugates of the invention generally involves functionalization, or activation, of the synthetic hydrophilic polymer. Although different synthetic hydrophilic synthetic polymers can be used in connection with forming the conjugate, the polymer must be biocompatible, hydrophilic, but relatively insoluble in water, and is preferably one or more forms of derivatized polyethylene glycol (PEG), due to its known biocompatibility. Various forms of derivatized PEG are extensively used in the modification of biologically active molecules because PEG can be formulated to have a wide range of solubilities and because it lacks toxicity, antigenicity, immunogenicity, and does not typically interfere with the enzymatic activities and/or conformations of peptides. Furthermore, PEG is generally non-biodegradable and is easily excreted from most living organisms including humans.

Various functionalized polyethylene glycols have been used effectively in fields such as protein modification (see Abuchowski et al., *Enzymes as Drugs,* John Wiley & Sons: New York, N.Y. (1981) pp. 367–383; and Dreborg et al., *Crit. Rev. Therap. Drug Carrier Syst.* (1990) 6:315), peptide chemistry (see Mutter et al., *The Peptides,* Academic: New York, N.Y. 2:285–332; and Zalipsky et at., *Int. J. Peptide Protein Res.* (1987) 30:740), and the synthesis of polymeric drugs (see Zalipsky et al., *Eur. Polym. J.* (1983) 19:1177; and Ouchi et al., *J. Macromol. Sci.-Chem.* (1987) A24:1011). Various types of conjugates formed by the binding of activated (functionalized) polyethylene glycol with specific pharmaceutically active proteins have been disclosed and found to have useful medical applications in part due to the stability of such conjugates with respect to proteolytic digestion, reduced immunogenicity, and longer half-lives within living organisms.

One form of polyethylene glycol which has been found to be particularly useful is monomethoxy-polyethylene glycol (mPEG), which can be activated by the addition of a compound such as cyanuric chloride, then coupled to a protein (see Abuchowski et al., *J. Biol. Chem.* (1977) 252:3578). Although such methods of activating polyethylene glycol can be used in connection with the present invention, they are not preferred in that the cyanuric chloride is relatively toxic and must be completely removed from any resulting product in order to provide a pharmaceutically acceptable composition.

Activated forms of PEG, including activated forms of mPEG, can be made from reactants which can be purchased commercially. One form of activated PEG which has been found to be particularly useful in connection with the present invention is mPEG-succinate-N-hydroxysuccinimide ester (SS-PEG) (see Abuchowski et at., *Cancer Biochem. Biphys.* (1984) 7:175). Activated forms of PEG such as SS-PEG react with the proteins under relatively mild conditions and produce conjugates without destroying the specific biological activity and specificity of the protein attached to the PEG. However, when such activated PEGs are reacted with proteins, they react and form linkages by means of ester bonds. Although ester linkages can be used in connection with the present invention, they are not particularly preferred in that they undergo hydrolysis when subjected to physiological conditions over extended periods of time (see Dreborg et al., *Crit. Rev. Therap. Drug Carrier Syst.* (1990) 6:315; and Ulbrich et al., *J. Makromol. Chem.* (1986) 187:1131).

It is possible to link PEG to proteins via urethane linkages, thereby providing a more stable attachment which is more resistant to hydrolytic digestion than the ester linkages (see Zalipsky et al., Polymeric Drug and Drug Delivery Systems, Chapter 10, "Succinimidyl Carbonates of Polyethylene Glycol" (1991)). The stability of urethane linkages has been demonstrated under physiological conditions (see Veronese et al., *Appl. Biochem. Biotechnol.* (1985) 11:141; and Larwood et al., *J. Labelled Compounds Radiopharm.* (1984) 21:603). Another means of attaching the PEG to a protein can be by means of a carbamate linkage (see Beauchamp et al., *Anal. Biochem.* (1983) 131:25; and Berger et al., *Blood* (1988) 71:1641). The carbamate linkage is created by the use of carbonyldiimidazole-activated PEG. Although such linkages have advantages, the reactions are relatively slow and may take 2 to 3 days to complete.

The various means of activating PEG described above and publications cited in connection with the activation means are described in connection with linking the PEG to specific biologically active proteins and not inert, biologically inactive, natural polymers such as collagen. (See *Polymeric Drug and Drug Delivery Systems,* Chapter 10, "Succinimidyl Carbonates of Polyethylene Glycol" (1991).) However, the present invention now discloses that such activated PEG compounds can be used in preparation of covalently crosslinked conjugates of various chemically modified collagens to provide a conjugate having sufficient optical characteristics, such as optical clarity, that the conjugate can be used to form various compositions for use in ophthalmic and other medical applications.

Another difunctionally activated form of PEG is referred to as PEG succinimidyl (S-PEG). The structural formula for this compound and the reaction product obtained by reacting it with a chemically modified collagen such as methylated collagen is shown in Formula. 2. In any general structural formula for the compounds, the subscript 3 is replaced with an "n". In the embodiment shown in Formula 1, n=3, in that there are three repeating $CH_2$ groups on either side of the PEG. The structure in Formula 2 results in a conjugate which includes an "ether" linkage which is not subject to hydrolysis. This is distinct from the conjugate shown in Formula 1, wherein an ester linkage is provided. The ester linkage is subject to hydrolysis under physiological conditions.

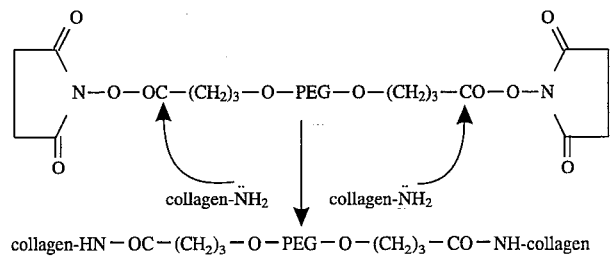

S-PEG, n = 3: Difunctionally Activated PEG Succinimidyl

S-PEG, n = 3: Difunctional PEG Succinimidyl                    FORMULA 2

Specific Forms of Activated PEG

For use in the present invention, polyethylene glycol is modified in order to provide activated groups on one or, preferably, two or more sites along the length of the PEG molecule, so that covalent binding can occur between the PEG and the free amino groups on a chemically modified collagen molecule. Some specific activated forms of PEG are shown structurally below, as are generalized reaction products obtained by reacting activated forms of PEG with chemically modified collagens. In Formulas 1–7, the term COLLAGEN is used to represent various forms of chemically modified collagens, such as succinylated collagen, methylated collagen, and deamidated collagen, for example. The term PEG is used to represent polymers having the repeating structure $(CH_2CH_2OCH_2CH_2)_n$.

The first activated PEG is difunctionally activated PEG succinimidyl glutarate, referred to herein as (SG-PEG). The structural formula of this molecule and the reaction product obtained by reacting it with a chemically modified collagen are shown in Formula 1.

Yet another difunctionally activated form of polyethylene glycol, wherein n=2, is shown in Formula 3, as is the conjugate formed by reacting the activated PEG with a chemically modified collagen.

SG-PEG: Difunctionally Activated PEG Succinimidyl Glutarate

S-PEG: Difunctional PEG Succinimidyl Glutarate                FORMULA 1

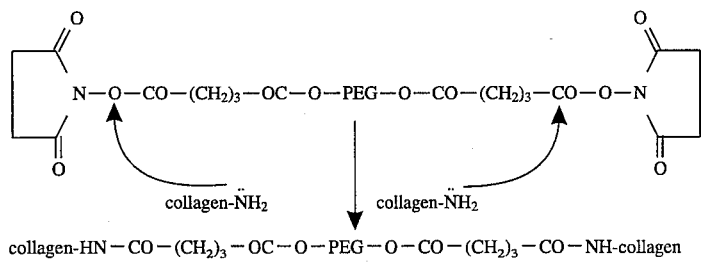

S-PEG, n = 2: Difunctionally Activated PEG Succinimidyl

S-PEG, n = 2: Difunctional PEG Succinimidyl    FORMULA 3

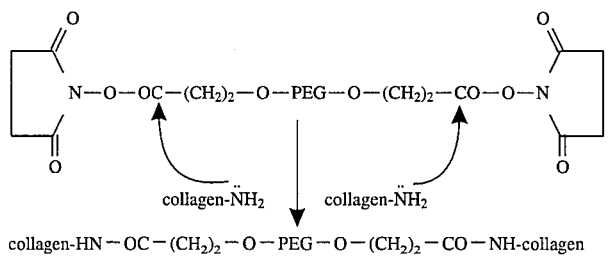

collagen-HN—OC—(CH$_2$)$_2$—O—PEG—O—(CH$_2$)$_2$—CO—NH-collagen

Another preferred embodiment of the invention similar to the compounds of Formulas 2 and 3 is provided when n=1. The structural formula and resulting chemically modified collagen-synthetic polymer conjugate are shown in Formula 4. It is noted that this conjugate includes both an ether and a peptide linkage. These linkages are stable under physiological conditions.

All of the activated polyethylene glycol derivatives depicted in Formulas 1–5 involve the inclusion of the succinimidyl group. However, different activating groups can be attached at sites along the length of the PEG molecule. For example, PEG can be derivatized to form difunctionally activated PEG propion aldehyde (A-PEG), which is shown in Formula 6, as is the conjugate formed by S-PEG, n = 1: Difunctionally Activated PEG Succinimidyl S-PEG, n = 1: Difunctional PEG Succinimidyl    FORMULA 4

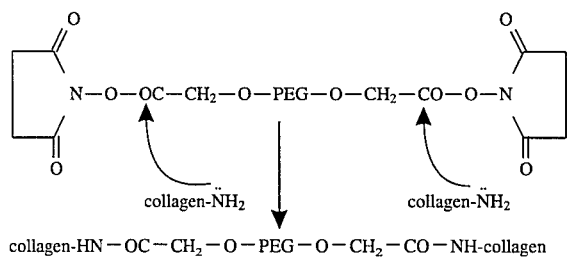

collagen-HN—OC—CH$_2$—O—PEG—O—CH$_2$—CO—NH-collagen

Yet another difunctionally activated form of PEG is provided when n=0. This compound is referred to as PEG succinimidyl carbonate (SC-PEG). The structural formula of this compound and the conjugate formed by reacting SC-PEG with a chemically modified collagen is shown in Formula 5.

the reaction of A-PEG with a chemically modified collagen. The linkage shown in Formula 6 is referred to as a —(CH$_2$)$_n$—NH— linkage, where n=1–10.

A-PEG: Difunctionally Activated PEG Propion Aldehyde

A-PEG: Difunctional PEG Propion Aldehyde    FORMULA 6

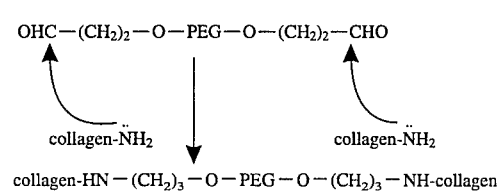

collagen-HN—(CH$_2$)$_3$—O—PEG—O—(CH$_2$)$_3$—NH-collagen

SC-PEG, n = 0;
Difunctionally Activated PEG Succinimidyl Carbonate

SC-PEG, n = 0: Difunctional PEG Succinimidyl Carbonate    FORMULA 5

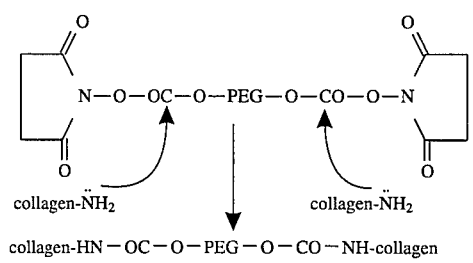

collagen-HN—OC—O—PEG—O—CO—NH-collagen

Yet another form of activated polyethylene glycol is difunctionally activated PEG glycidyl ether (E-PEG), which is shown in Formula 7, as is the conjugate formed by reacting such with a chemically modified collagen.

E-PEG: Difunctionally Activated PEG Glycidyl Ether

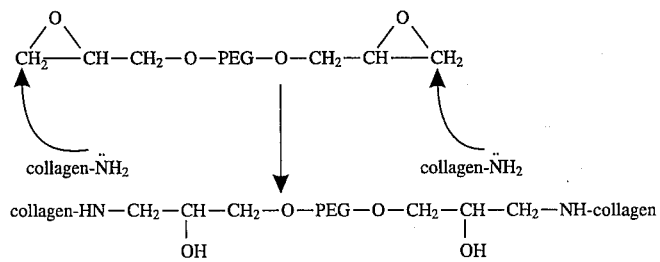

FORMULA 7

Crosslinking of Chemically Modified Collagen with PEG

Chemically modified collagens which have free amino groups can be covalently crosslinked by mixing with an appropriate amount of a multifunctionally (preferably difunctionally) activated synthetic hydrophilic polymer such as an activated polyethylene glycol. Chemically modified collagens retain their optical clarity after crosslinking with PEG to form clear gels having improved mechanical strength.

Covalently bound chemically modified collagen-synthetic polymer conjugates are formed within minutes of combining the chemically modified collagen with the functionally activated polymer. The chemically modified collagen can be mixed with the activated polymer using syringe-to-syringe mixing. Alternatively, the chemically modified collagen can be extruded into a solution of the activated polymer; crosslinking will occur as the polymer diffuses into the collagen. For crosslinking to occur between the synthetic polymer and the collagen, the pH of the reaction mixture must be maintained between approximately 6 and approximately 9.

The rate of conjugate formation and the characteristics of the resulting conjugate can be varied by varying the type of activated polymeric glycol used and/or the molecular weight and concentration of the polymeric glycol. In general, the use of polymeric glycol species (such as S-PEG) which result in ether or urethane linkages lead to the creation of more stable conjugates than those which result in the readily hydrolyzed ester linkages. Conjugates containing ether linkages are generally preferred for use in ophthalmic devices and materials intended for long-term use in vivo, such as lenticules. However, in certain situations, such as drug delivery applications, it is desirable to include the weaker ester linkages: the linkages are gradually broken by hydrolysis under physiological conditions, breaking apart the matrix and releasing the pharmaceutically active component held therein. Articles such as corneal shields where separation of the drug from the collagen-synthetic polymer matrix is required would generally incorporate weaker linkages such as ester linkages. Different species of polymeric glycols can be mixed and used in the same drug delivery composition, resulting in a varied rate of matrix degradation and, hence, drug release.

The specific concentration of activated polymeric glycol used will vary depending on the kind of polymeric glycol and the type of chemically modified collagen used, but is typically within the range of between about 1 to about 400 milligrams of polymeric glycol per milliliter of chemically modified collagen-synthetic polymer composition. For example, the preferred polymeric glycol concentration for preparing the optically clear compositions of the invention is in the range of from about 5 to about 70 milligrams of PEG per milliliter of succinylated collagen-synthetic polymer composition, and between about 1 to about 50 milligrams of PEG per milliliter of methylated collagen-synthetic polymer composition. The collagen concentration of the chemically modified collagen-synthetic polymer compositions is typically within the range of about 5 to about 120 mg/ml, depending on the physical properties required for the desired end use of the composition.

In one preferred embodiment, for example, 10 mg of a difunctionally activated polyethylene glycol is dissolved in 0.1 ml of PBS to make a crosslinker solution. The 0.1 ml of crosslinker solution is then mixed with, for example, 0.9 ml of succinylated collagen having a collagen concentration of 30 mg/ml. The total volume of the succinylated collagen-synthetic polymer composition is now 1.0 ml. The final composition contains a total of 10 mg of difunctionally activated S-PEG and 27 mg of succinylated collagen (0.9 ml×30 mg/ml collagen concentration).

The amount of activated polymeric glycol used and, hence, the degree of crosslinking will also vary depending on the desired end use of the material produced. For example, conjugates for use as vitreous gel replacements will need to be in a more fluid form, and thus require lighter crosslinking, than conjugates for use in solid implants, such as lenticules, which require formation of a firm, yet elastic gel. Presently preferred PEGs include difunctionally activated PEG succinimidyls (S-PEG), wherein n=0, 1, 2, 3, or 4, as depicted in Formulas 2–4. The physical form (e.g., solid implant, viscous gel) of the resulting chemically modified collagen-synthetic polymer compositions made using a difunctionally activated S-PEG will depend upon the relative amount of S-PEG used in the composition.

Multifunctionally activated polymeric glycols can be used to crosslink more than one chemically modified species of collagen. The resulting composite material will have different physical and chemical properties than conjugates involving only one species of chemically modified collagen.

Multifunctionally activated synthetic polymers may further be used to crosslink chemically modified collagen to other proteins such as growth factors or cytokines to produce compositions particularly suited for use in wound healing and immune modulation. Such tethering of cytokines or growth factors to chemically modified collagen provides an effective sustained release drug delivery system. Further, tethered cytokines can be used to anchor the composition in place, providing increased useful lifetime for the implant.

Compositions of the invention containing biologically active cytokines or growth factors such as TGF-β are prepared by admixing an appropriate amount of the cytokine or growth factor into the composition, or by incorporating the cytokine or growth factor into the chemically modified collagen prior to reaction with an activated polymeric glycol. Preferably, the cytokine or growth factor is first reacted with a molar excess of a multifunctionally activated polymeric glycol in a dilute solution for three to four minutes. The cytokine or growth factor is preferably provided at a concentration of about 1 µg/mL to about 5 mg/mL, while the activated polymer is preferably added to a final concentration providing a thirty- to fifty-fold molar excess. The conjugated biologically active factor-synthetic polymer is then added to an aqueous solution of chemically modified collagen (preferably having a concentration within the range of about 1 to about 60 mg/mL) at neutral pH (approximately 7–8) and allowed to react further to form biologically active factor-synthetic polymer-chemically modified collagen conjugates. The resulting composition is allowed to stand overnight at ambient temperature. The pellet is collected by centrifugation and washed with PBS, using vigorous vortexing to remove unbound factor. Methods for conjugating growth factors and cytokines to the collagen-polymer conjugate are further described in U.S. Pat. No. 5,162,430, which is incorporated herein by reference.

Use and Administration

Compositions comprising the chemically modified collagen-synthetic polymer conjugates of the present invention are generally used to form various ophthalmic devices, but can be used in the formation of a wide variety of materials used in connection with medical treatment. The conjugate formulations of the invention are particularly advantageous in that they provide materials and devices which are relatively transparent to visible light. Accordingly, the advantages of the present invention become more apparent when the invention is used to form a device for which optical clarity is a requirement.

Due to their optical clarity (greater than 90% transmittance of light at a wavelength of about 410 nm for an article having a thickness of 1 mm) and moldability, the conjugates are ideal for use in various materials and devices to be incorporated in the eye. For instance, they can be used as vitreous humor replacements, as corneal shields to deliver drugs to the eye, or as artificial corneal implants. As such, the conjugates can be used to deliver various drugs and therapeutic agents, such as TGF-β, antiglaucoma agents, steroids, antibiotics, to both the anterior and posterior chambers of the eye, depending on the desired therapeutic effect. As described above, the therapeutic agents may either be admixed with the chemically modified collagen-synthetic polymer conjugates or covalently bound to the conjugates.

Alternatively, the chemically modified collagen-synthetic polymer conjugates can be used as starting materials in the procedure for synthetic epikeratoplasty. As such, the conjugates are shaped into preformed lenticules. The corneal epithelium is removed and the lenticule is attached to the cornea by means of various bonding agents or tissue adhesives, including any suitable biocompatible adhesive, such as fibrin glue. In an alternative procedure, the preformed collagen-polymer lenticule is surgically implanted by means of a shallow peripheral groove or slit formed in the cornea. The lenticule is then shaped by laser ablation to achieve the desired refractive correction. The corneal epithelium generally grows back over the surface of the lenticule within three days following the procedure. Growth factors may be incorporated into the composition to facilitate regrowth of the corneal epithelium and/or healing of the corneal surface if a surgical incision is required. Various alternative techniques for this procedure are described in U.S. Pat. Nos. 4,923,467 and 5,156,622, incorporated herein by reference.

In a similar procedure, following removal of the corneal epithelium, the chemically modified collagen and activated synthetic polymer are mixed and immediately delivered as a thin layer (approximately 150 to 200 microns) directly to the surface of the Bowman's layer of the cornea. The chemically modified collagen and activated polymer covalently crosslink in situ to form a lenticule on the surface of the cornea. Thus formed, the lenticule attaches directly to the de-epithelialized cornea. Following curing, the material can be laser ablated to achieve the desired refractive correction, as set forth in U.S. Pat. Nos. 5,163,956 and 5,196,027, incorporated herein by reference. As in the procedure described above using the preformed lenticule, regrowth of the corneal epithelium occurs within days of the procedure. Again, incorporation of growth factors into the composition may facilitate regrowth of the corneal epithelium over the lenticule.

Due to their mechanical strength and elasticity, the conjugates of the invention are also useful in a variety of other medical and surgical applications. For example, the chemically modified collagen-synthetic polymer conjugates may be used as coatings for various medical devices for long-term incorporation into the body, molded into articles useful for repair or replacement of cartilage, ligaments, and tendons, or formed into tubes, as described in copending U.S. application Ser. No. 07/985,680, for use as vascular grafts and stents or in nerve repair.

EXAMPLES

The following examples are put forth so as to provide those of ordinary skill in the art with a complete disclosure and description of how to make the conjugates, compositions, and devices and are not intended to limit the scope of what the inventors regard as their invention. Efforts have been made to ensure accuracy with respect to numbers used (e.g., amounts, temperature, molecular weight, etc.) but some experimental errors and deviation should be accounted for. Unless indicated otherwise, parts are parts by weight, molecular weight is weight average molecular weight, temperature is in degrees Centigrade, and pressure is at or near atmospheric.

Example 1

(Preparation of PEG Crosslinked Succinylated Collagen)

Six (6) liters of collagen-in-solution (CIS) (3 mg/ml collagen in pH 2 HCl) was adjusted to pH 9 using 0.1M NaOH at room temperature to produce fibrillar collagen. 1.35 grams of succinic anhydride powder was added to the fibrillar collagen and the pH maintained between 8.5 and 9, resulting in the formation of succinylated collagen. The pH of the succinylated collagen was adjusted to 7.2, then to 4.2 using 0.1M HCl to precipitate the succinylated collagen. The succinylated collagen was then centrifuged mid the supernatant discarded. The pH of the pellet was adjusted to 7.2 using 0.1M NaOH. The succinylated collagen pellet was diluted in water and the collagen concentration of the resulting succinylated collagen solution determined to be 20 mg/ml.

Solutions of difunctionally activated S-PEG in PBS were prepared at different concentrations as follows: 10 mg S-PEG in 0.1 ml PBS, 20 mg S-PEG in 0.1 ml PBS, 50 mg S-PEG in 0.1 ml PBS, and 100 mg S-PEG in 0.2 ml PBS. Each of the four crosslinker solutions was mixed with 0.9 ml of the 20 mg/ml succinylated collagen using syringe-to-syringe mixing. The four succinylated collagen—S-PEG compositions had final S-PEG concentrations of 10, 20, 50, and 91 mg/ml, respectively. The final collagen concentration of the samples, was approximately 18 mg/ml.

The four formulations were observed visually for signs of crosslinking at 5 minutes and 2 hours after mixing. As shown in Table 1, the succinylated collagen formulations containing 50 and 91 mg/ml S-PEG showed signs of crosslinking 5 minutes after mixing. All four formulations showed significant crosslinking 2 hours after mixing, forming optically clear gels.

philized and dialyzed and the collagen concentration was adjusted to 20 mg/ml by the addition of 0.02M $Na_2HPO_4$/ 0.13M NaCl, pH 7.3.

Solutions of difunctionally activated S-PEG in PBS were prepared at different concentrations as follows: 3 mg S-PEG in 0.15 ml PBS, 9 mg S-PEG in 0.15 ml PBS, 15 mg S-PEG in 0.15 ml PBS, 30 mg S-PEG in 0.15 ml PBS, 45 mg S-PEG in 0.15 ml PBS, 75 mg S-PEG in 0.15 ml PBS, 111 mg S-PEG in 0.2 ml PBS, and 165 mg S-PEG in 0.2 ml PBS. Each of the crosslinker solutions was mixed with 1.35 ml of the 20 mg/ml methylated collagen using syringe-to-syringe mixing. The methylated collagen—S-PEG compositions had final S-PEG concentrations of 2, 6, 10, 20, 30, 50, 72, and 106 mg/ml, respectively. The final collagen concentration of the samples was approximately 18 mg/ml.

The resulting formulations were evaluated qualitatively for elasticity and gel strength. As shown in Table 2, the

TABLE 1

PEG Crosslinking of Succinylated Collagen

| SPEG (mg) | PBS (ml) | Succinylated Collagen (ml) | Signs of Crosslinking? (5 minutes) | Signs of Crosslinking? (2 hours) | Final S-PEG Conc. (mg/ml) |
|---|---|---|---|---|---|
| 10 | 0.1 | 0.9 | no | yes | 10 |
| 20 | 0.1 | 0.9 | no | yes | 20 |
| 50 | 0.1 | 0.9 | some signs | yes | 50 |
| 100 | 0.2 | 0.9 | some signs | yes | 91 |

The melting temperatures of the succinylated collagen formulations containing 10, 20, 50, and 91 mg/ml S-PEG (Samples B, C, and D, respectively) were measured using differential scanning calorimetry (DSC) and compared with that of noncrosslinked succinylated collagen (Sample A). DSC is a measure of degree of crosslinking which is commonly used to evaluate gel stability.

DSC results are shown in FIG. 1. The melting temperatures for the crosslinked formulations (B, C, and D) were significantly higher than that for the noncrosslinked succinylated collagen (A).

Example 2

(Preparation of PEG Crosslinked Methylated Collagen)

Ninety (90) milliliters of Zyderm® II Collagen without lidocaine (Collagen Corporation, Palo Alto, Calif.), adjusted to 20 mg/ml collagen concentration, was lyophilized to form freeze-dried collagen. The freeze-dried collagen was then chopped into small pieces.

8.3 milliliters of concentrated hydrochloric acid and 30 grams of sodium sulfate were added to methanol to produce anhydrous acidic methanol. The sodium sulfate was then filtered off of the anhydrous acidic methanol. Approximately 1 liter of the acidified anhydrous methanol was subsequently mixed with the chopped freeze-dried collagen.

After incubation at room temperature for 7 days, methylated collagen was formed. The excess methanol was evaporated off. The resulting material was subsequently lyoformulations containing 30 and 50 mg/ml S-PEG showed signs of crosslinking immediately upon mixing. The compositions containing 2, 6, 10, and 20 mg/ml S-PEG required approximately 5 to 10 minutes for crosslinking. The compositions containing 72 and 106 mg/ml S-PEG required longer than 10 minutes for gel formation, forming weak, inelastic gels. The compositions containing between 2–20 mg/ml S-PEG resulted in the strongest, most elastic gels. The composition containing 30 mg/ml S-PEG formed a gel with good strength, but low elasticity, which could be useful in applications where elasticity is not a desired characteristic. Compositions of methylated collagen containing greater than 30 mg/ml S-PEG showed poor elasticity and gel strength. All gels were optically clear.

Figure 2:
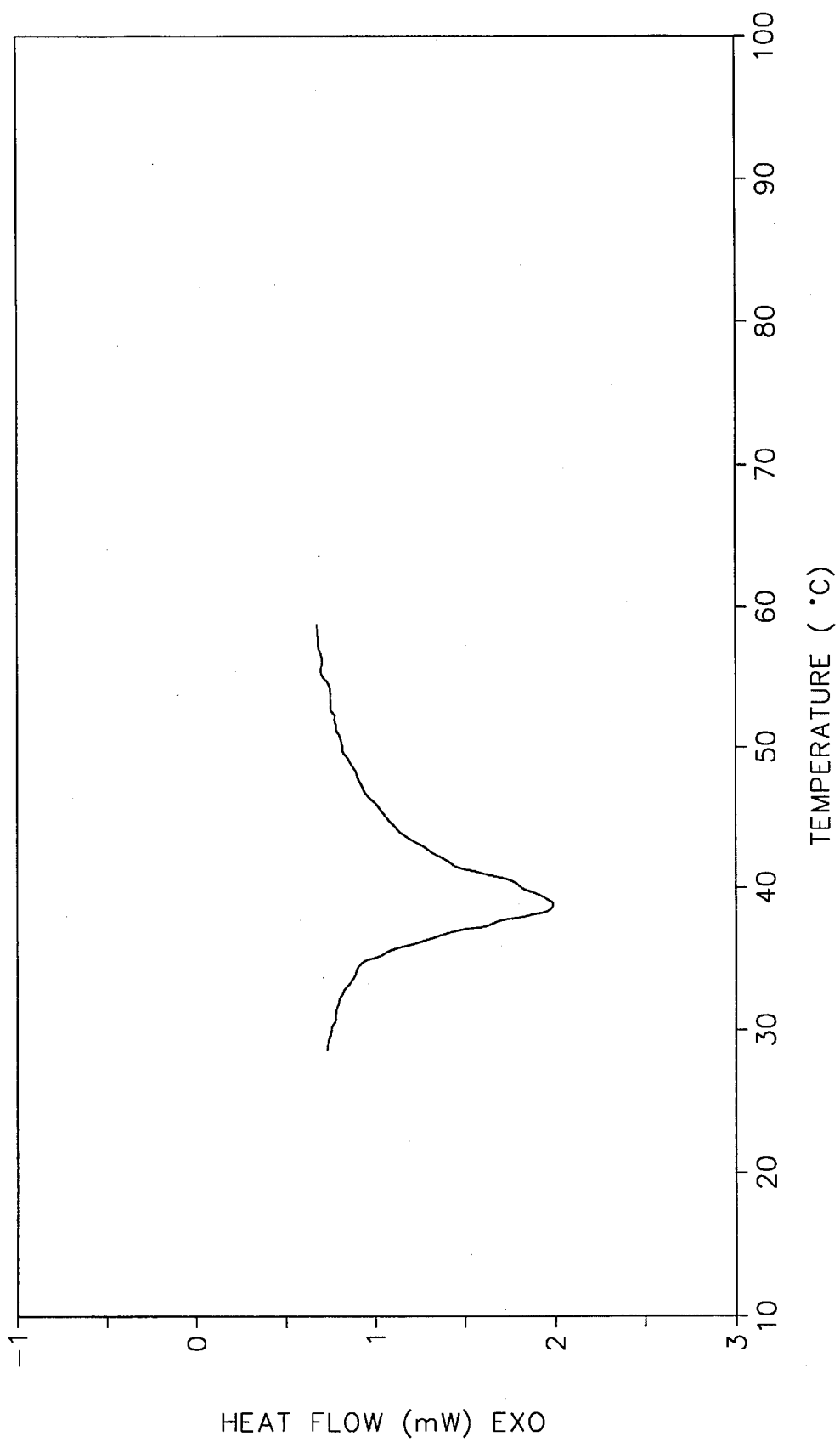
FIG. 2 shows DSC results for methylated collagen formulations containing 2, 10, 30, and 72 mg/ml S-PEG (Samples E, F, G, and H, respectively).
Figure 3:
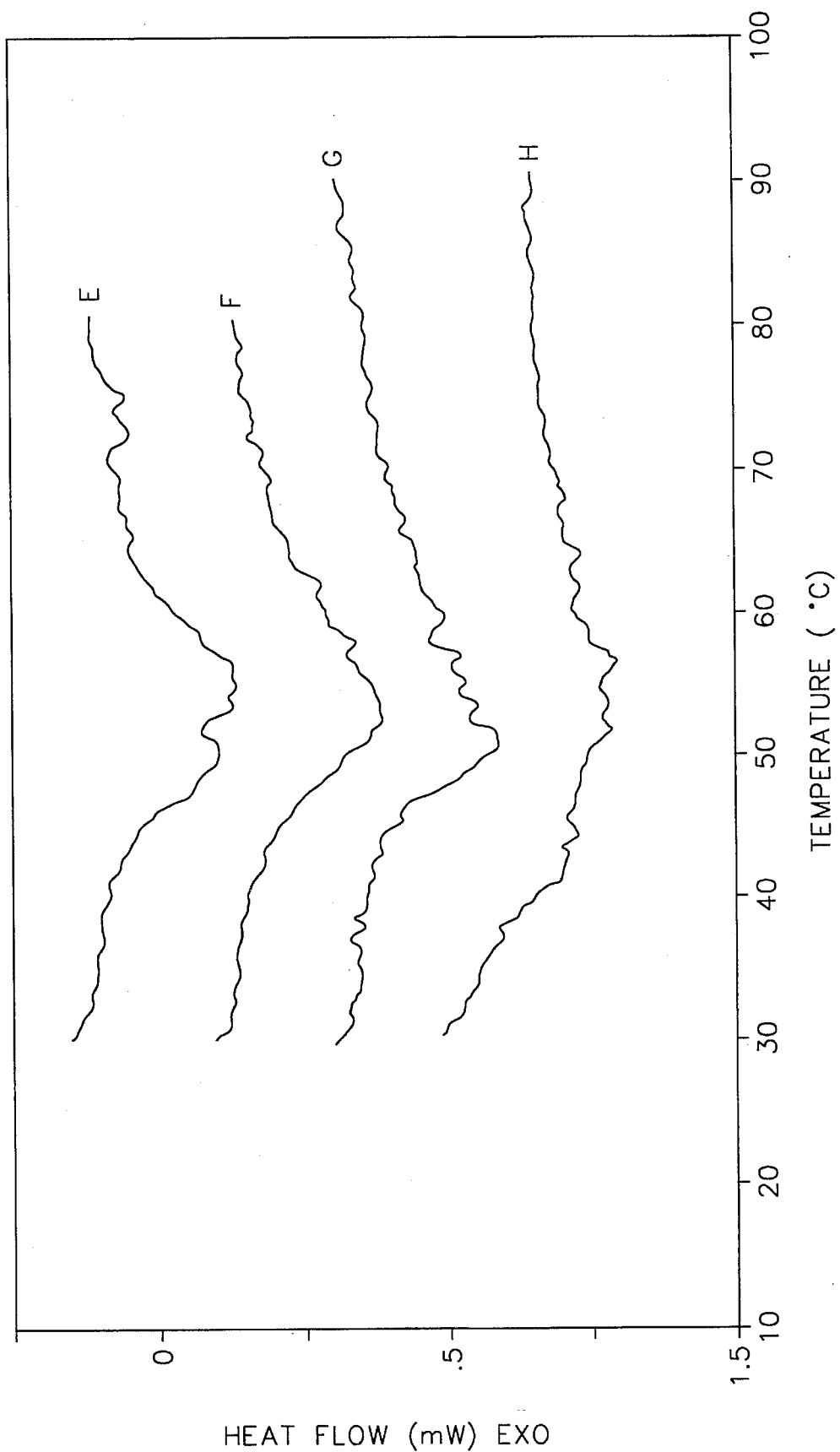
FIG. 3 shows DSC results for noncrosslinked methylated collagen.

The melting temperatures of the methylated collagen formulations containing 2, 10, 30, and 72 mg/ml S-PEG (Samples E, F, G, and H respectively) were measured using differential scanning calorimetry (DSC) and compared with that of noncrosslinked methylated collagen. The DSC results for the noncrosslinked and crosslinked samples are shown in FIGS. 2 and 3, respectively. The melting curve profiles indicate that the crosslinked formulations contain a heterogeneous population of molecules, most of which melt at a higher temperature than the noncrosslinked collagen.

As shown in Table 2, the melting temperatures for the crosslinked formulations were significantly higher than that for the noncrosslinked methylated collagen.

TABLE 2

| | PEG Crosslinking of 20 mg/ml Methylated Collagen | | | |
|---|---|---|---|---|
| Final S-PEG Conc. (mg/ml) | Time to Form Gel | Elasticity | Gel Strength | DSC Tm (°C.) Range |
| 0 | — | — | — | 38–43 |
| 2 | 5–10 min. | elastic | good | 45–60 |
| 6 | 5–10 min. | elastic | good | — |
| 10 | 5–10 min. | very elastic | very good | 45–68 |
| 20 | 5 min. | slightly elastic | good | — |
| 30 | immediate | not elastic | good | 47–62 |
| 50 | immediate | slightly elastic | not good | — |
| 72 | >10 min. | not elastic | not good | 40–70 |
| 106 | >10 min. | not elastic | not good | — |

Example 3

(In vitro Delivery & Attachment of in situ Polymerizable Lenticule to Bovine Cornea)

Methylated collagen having a collagen concentration of 30 mg/ml was prepared as described in Example 2. The epithelial layer of the cornea of an excised bovine eye was removed using a blunt metal spatula. Following de-epithelialization, the cornea was washed with PBS and dried thoroughly using a sponge.

A solution of 10 mg difunctionally activated S-PEG in 0.1 ml PBS was prepared. The crosslinker solution was mixed with 0.9 ml of the 30 mg/ml methylated collagen using syringe-to-syringe mixing. Immediately following mixing, approximately 0.2 ml of the methylated collagen—S-PEG material was extruded from the opening of the 1.0 cc syringe onto the surface of the de-epithelialized bovine cornea.

The methylated collagen—S-PEG material was molded in place on the cornea using a polymethylmethacrylate (PMMA) mold. Crosslinking and gel formation of the collagen-polymer occurred within approximately three minutes to form a lenticule in situ on the bovine cornea.

Following gel formation, the mold was removed from the collagen-polymer material. The surface of the in situ formed lenticule was irrigated with PBS. The lenticule was secure and not dislodged by the irrigation. Gentle teasing of the lenticule with a spatula indicated that it was favorably attached to the cornea. The lenticule was able to be removed by "peeling" with a spatula.

Histological examination (at 100× magnification) was performed on the bovine cornea before and after removal of the methylated collagen—S-PEG lenticule. Histological examination before lenticule removal indicated an intimate interface between the lenticule and the cornea. Following lenticule removal, the surface of the: cornea showed no obvious damage or aberrations.

The above experiment was repeated using a material prepared from succinylated collagen, at a 36% level of succinylation and a 30 mg/ml collagen concentration. Twenty (20) milligrams of difunctionally activated S-PEG was dissolved in 0.1 ml PBS. The crosslinker solution was subsequently mixed with 0.9 mg of the 30 mg/ml succinylated collagen using syringe-to-syringe mixing, then delivered to a de-epithelialized bovine cornea. Gel formation occurred within approximately 10 minutes following delivery of the collagen-polymer material to the cornea. Qualitative comparison revealed the methylated collagen—S-PEG material to have better attachment to the cornea than the succinylated collagen—S-PEG material.

The present invention is shown and described herein at what is considered to be the most practical, and preferred embodiments. It is recognized, however, that departures may be made therefrom which are within the scope of the invention and that obvious modifications will occur to one skilled in the art upon reading this disclosure.

What is claimed:

1. A conjugate comprising a synthetic hydrophilic polymer covalently bound to a chemically modified collagen which is in substantially nonfibrillar form at pH 7 selected from the group consisting of succinylated collagen, methylated collagen, and mixtures thereof.

2. The conjugate of claim 1, wherein the synthetic hydrophilic polymer is an activated polymeric glycol.

3. A conjugate of claim 2, wherein the activated polymeric glycol is a difunctionally activated polyethylene glycol.

4. The conjugate of claim 1, wherein the chemically modified collagen is succinylated collagen having a level of succinylation within the range of between about 25% and about 50% available lysine residues succinylated.

* * * * *